United States Patent
Alec

(10) Patent No.: US 8,500,820 B2
(45) Date of Patent: Aug. 6, 2013

(54) BONE CEMENT COLLECTOR AND METHOD OF USE

(75) Inventor: Birkbeck Alec, Leeds (GB)

(73) Assignee: Depuy International Limited (GB)

( * ) Notice: Subject to any disclaimer, the term of this patent is extended or adjusted under 35 U.S.C. 154(b) by 165 days.

(21) Appl. No.: 12/995,321

(22) PCT Filed: Apr. 7, 2009

(86) PCT No.: PCT/GB2009/000903
§ 371 (c)(1), (2), (4) Date: Jan. 3, 2011

(87) PCT Pub. No.: WO2009/144440
PCT Pub. Date: Dec. 3, 2009

(65) Prior Publication Data
US 2011/0112653 A1    May 12, 2011

(30) Foreign Application Priority Data
May 31, 2008 (GB) .................... 0809958.2

(51) Int. Cl.
*A61F 2/28* (2006.01)
(52) U.S. Cl.
USPC ...................................... 623/23.48
(58) Field of Classification Search
USPC ...................................... 623/23.48
See application file for complete search history.

(56) References Cited

U.S. PATENT DOCUMENTS

| | | | | |
|---|---|---|---|---|
| 4,020,558 | A | * | 5/1977 | Cournut et al. .................. 433/80 |
| 4,718,909 | A |  | 1/1988 | Brown |
| 5,913,899 | A | * | 6/1999 | Barrett et al. .............. 623/23.41 |
| 5,951,563 | A |  | 9/1999 | Brown |
| 6,264,698 | B1 |  | 7/2001 | Lawes |
| 2007/0276399 | A1 | * | 11/2007 | Medley et al. .................. 606/92 |
| 2008/0015708 | A1 | * | 1/2008 | Howie et al. .............. 623/23.22 |

FOREIGN PATENT DOCUMENTS

| | | |
|---|---|---|
| EP | 616796 A1 | 9/1994 |
| EP | 916324 B1 | 5/1999 |
| WO | WO 9510990 A1 | 4/1995 |
| WO | WO 0110356 A2 | 2/2001 |

OTHER PUBLICATIONS

UK Search Report GB0809958.2, Nov. 25, 2008.
PCT International Search Report PCT/GB2009/000903, Aug. 3, 2009.

* cited by examiner

*Primary Examiner* — David Isabella
*Assistant Examiner* — Randy Shay

(57) ABSTRACT

A bone cement collector includes a body having a structure that is permeable to bone cement and has opening for trapping bone cement. The body is releasably attached to an orthopaedic implant component at a location on the implant at which bone cement is likely to escape during positioning of the orthopaedic implant.

16 Claims, 3 Drawing Sheets

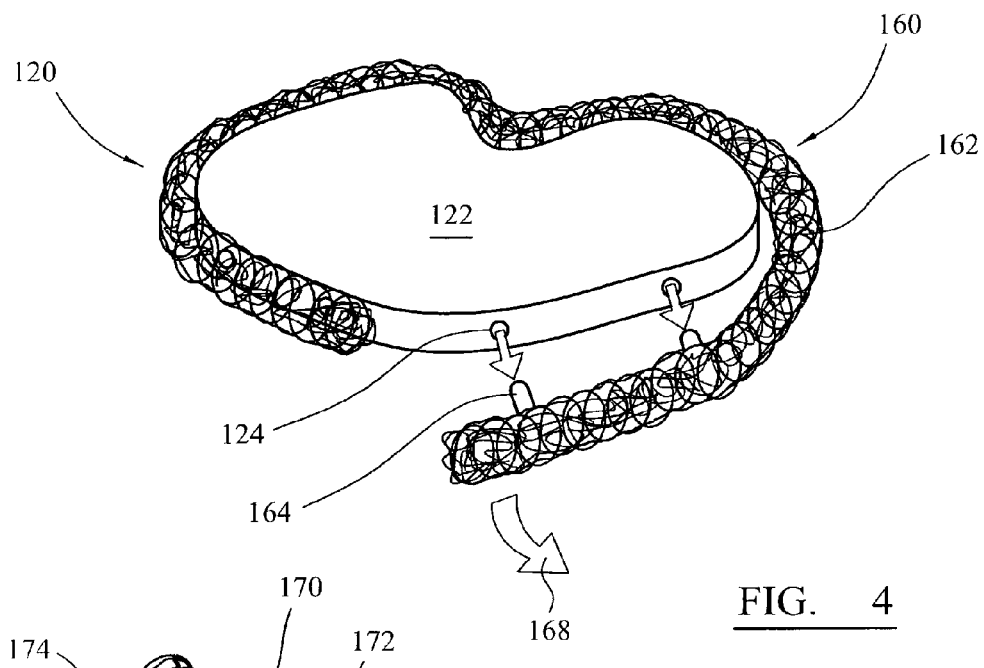
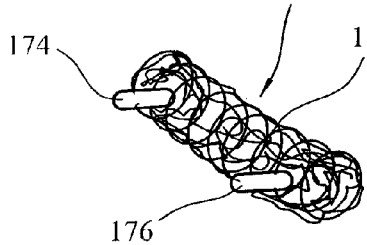
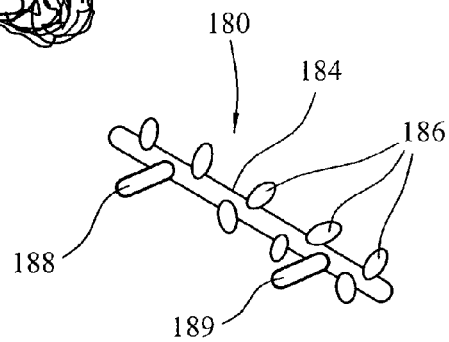
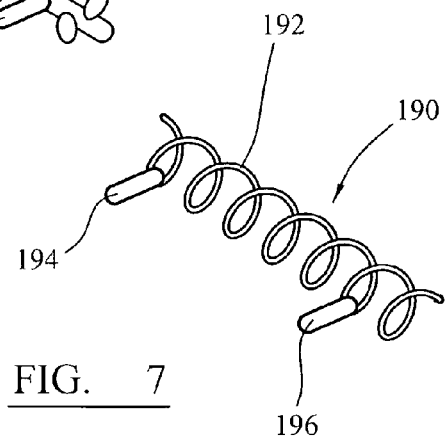
FIG. 4
FIG. 5
FIG. 6
FIG. 7

BONE CEMENT COLLECTOR AND METHOD OF USE

CROSS REFERENCE TO RELATED APPLICATION

This application is a national stage application under 35 U.S.C. 371 of International Patent Application PCT/GB2009/000903 filed Apr. 7, 2009.

The present invention relates generally to the field of bone cement and in particular to methods and apparatus for handling excess bone cement during an orthopaedic arthroplasty procedure.

BACKGROUND OF THE INVENTION

Bone cement is used during many orthopaedic arthroplasty procedures in order to securely attach the arthroplasty implant to the patient's bone. It is of vital importance to ensure that sufficient cement is applied to ensure good interlock. The amount of interlock depends on a number of factors such as pressurisation, bone density and any cavities present. These factors currently require the surgeon to apply more cement than is actually required. If too little cement is used, then the implant may fail by becoming partially or wholly detached from the bone. This may require revision surgery, if there is sufficient remaining bone stock, or some other remedial procedure.

It can also be important to ensure that the bone cement is used when it is at the correct consistency as it cures. If the cement is used too soon during its cure, then the cement can be too runny and may leak off the bone. If the cement is used too late during its cure, then its adhesive properties in securing the implant to the bone may be impaired and an insufficiently strong fixation may occur. Hence, there is also a window of time during which cement should be used. However, there is great demand for orthopaedic surgery procedures and surgeons do not have time to wait during the procedure to ensure that the cement is at the perfect point in its cure either in terms of its ease of handling or its adhesive properties for application to the bone.

If too much cement is placed on the bone then when the implant is placed, the implant often squeezes cement away from the bone at the edges and the cement tends to become trapped in and around the patient's joint. Similarly if the cement is too runny, the cement can run off the bone and accumulate in and around the patient's joint. Hence, the surgeon often has to spend considerable time and skill trying to clean excess cement from on and around the implant and joint using curettes, scalpels or by hand. Otherwise, the cement, when dried, will harm the patient and may require surgical intervention to remove. It can be particularly difficult to ensure that all cement is removed as often there is very limited access to the joint. For example if may be necessary to try and remove cement from behind a knee joint and access to that space may be very limited. This is particularly the case during minimally invasive surgical procedures. Therefore, both the risk of leaving cement pieces in the joint and also scratching the implant surface is high.

Hence, apparatus and methods for improving the handling of bone cement during placement of an orthopaedic implant would be beneficial.

BRIEF SUMMARY OF THE INVENTION

The present invention provides apparatus and a method for quickly removing excess cement around an implant where the excess cement forms.

A first aspect of the invention provides a bone cement collector, comprising a body and a releasable attachment mechanism by which the body can be releasably attached to an orthopaedic implant component. The body can be attached at a location on the implant at which bone cement is caused or likely to be caused to escape during placement of the orthopaedic implant.

Hence, the body can act to collect excess cement displaced by the implant and can then be removed from the implant, taking the excess bone cement with it, thereby reducing or eliminating the need to remove excess cement after the implant has been placed.

The body can have a structure which is configured to be permeable to bone cement and/or to trap bone cement. The structure can be a foam or mesh or similar. The structure can be a support or substrate bearing a plurality of formations. The structure can be a single part or can comprise a plurality of parts. The structure can have a plurality of voids or apertures. The voids or apertures can present a tortuous fluid flow path. The structure can present a plurality of different and/or separate surfaces to which bone cement can adhere.

The releasable attachment mechanism can comprises an adhesive.

The releasable attachment mechanism can be a mechanical coupling. For example, the mechanical coupling can include a push-fit or snap-fit coupling or a plurality of push-fit or snap-fit couplings.

The releasable attachment mechanism comprises a suction coupling. The suction coupling can comprise a plurality of suction pads or cups disposed on a rear side of the collector. This provides a particularly suitable mechanism for attaching to the smooth surface of many implants.

The bone cement collector comprises a substrate bearing at least one formation or a plurality of formations defining a plurality of voids through which bone cement can pass.

The bone cement collector can comprise a substrate bearing at least one formation, or a plurality of formations, defining a plurality of separate or different surfaces or parts to which bone cement can adhere. This can help to retain the bone cement on the collector when removing the collector after the bone cement has been allowed to continue curing.

The bone cement collector can include at least one handle by which a user can pull to remove the bone cement collector. The handle can be attached to a free end of the collector. A handle can be provided at each free end of the or each collector.

A second aspect of the invention provides a bone cement controlling orthopaedic implant comprising: an orthopaedic implant component; and a bone cement collector according to any of the first aspects of the invention. The cement collector can be releasably attached to the orthopaedic implant component by the releasable attachment mechanism at a location on the implant at which bone cement is caused to escape during placement of the orthopaedic implant.

The bone cement collector can extend at least partially about an end or part of the component. The end of part of the component can be an end or part intended to face rearward when the component is implanted. This helps with removing excess cement from particularly inaccessible parts of a surgical site.

The bone cement collector can extend substantially entirely around the periphery of the component. This helps to collect all excess cement that might escape.

The implant can include a plurality of cement collectors releasably attached to the orthopaedic implant. Different types of cement collectors can be attached at different positions. This allows the implant to be customised for specific uses.

The implant can be any orthopaedic implant secured by bone cement, such as a knee implant, a hip implant or a shoulder implant. In particular, the implant can be a tibial implant, a femoral implant, a femoral stem or an acetabular cup.

A third aspect of the invention provides a method for handling bone cement during an orthopaedic arthroplasty procedure, comprising: applying bone cement to a prepared surface of a bone; placing an implant component having a bone cement collector releasably attached thereto on the bone cement; and removing the bone cement collector, and any or at least some cement attached thereto, from the implant component.

Removing the bone cement collector from the implant component can includes removing at least a portion of the bone cement collector from a rearward facing portion of the implant component.

BRIEF DESCRIPTION OF THE DRAWINGS

Embodiments of the invention will now be described in detail, by way of example only, and with reference to the accompanying drawings, in which:

FIG. 4 shows a perspective view of a further implant and cement collector according to the invention;

FIG. 5 shows a schematic perspective view of a cement collector according to the invention;

FIG. 6 shows a schematic perspective view of a further cement collector according to the invention;

FIG. 7 shows a schematic perspective view of a further cement collector according to the invention;

Similar items in different Figures share common reference signs unless indicated otherwise.

DETAILED DESCRIPTION OF THE INVENTION

Figure 1:
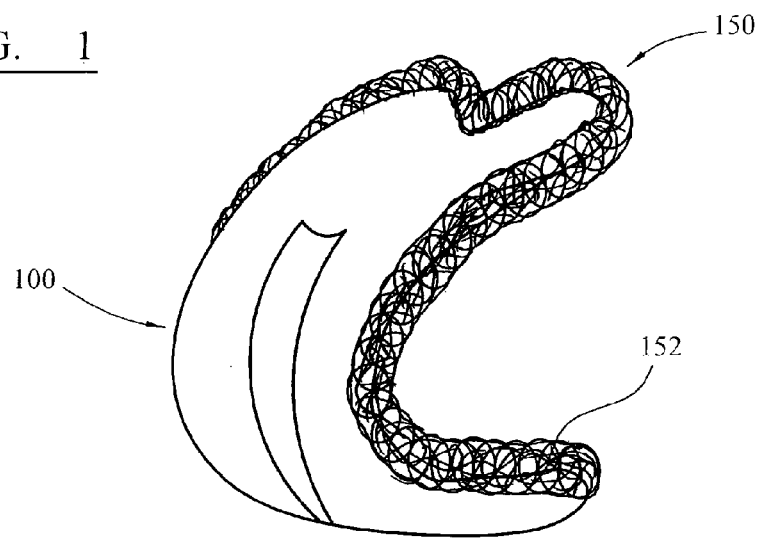
FIG. 1 shows a perspective view of an implant and cement collector according to the invention.
Figure 2:
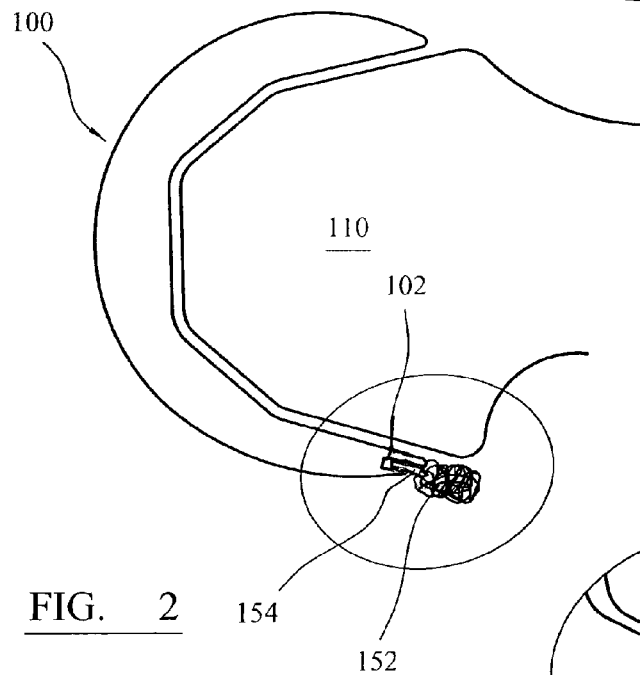
FIG. 2 shows a side view of the implant and cement collector of FIG. 1.

With reference to FIG. 1, there is shown a schematic perspective view of an implant 100 according to the invention and bearing a bone cement collector 150 also according to the invention. FIG. 2 shows a cross section through implant 100 when placed on a resected proximal end 110 of a femur. The implant 100 is a generally conventional femoral implant except that it has been adapted to have the bone cement collector 150 releasably attached thereto as will be described in greater detail below.

The bone cement collector 150 has a generally elongate body made of a plastic mesh 152 and having a flange or lip member 154 extending from the mesh. The flange or lip 154 is snugly received in a narrow channel 102 which extends around the periphery of the implant 150. The channel 102 and flange 154 are dimensioned so that the cement collector can be released from the implant in a tearing motion which extracts the flange from the channel. Hence, the channel and flange provide between them a releasable attachment mechanism by which the cement collector can be removed from the implant.

The mesh has a complex and convoluted structure which provides a plurality of voids. The mesh structure is chosen so that the voids are sufficiently large and common to allow bone cement to pass into or at least partially through the cement collector. That is the cement collector is at least partially permeable to bone cement. Further, the material of the mesh giving rise to its structure presents a plurality of members which help to trap bone cement within or on the cement collector and which also provide a plurality or surfaces to which the bone cement can at least partially adhere in use.

Figure 3:
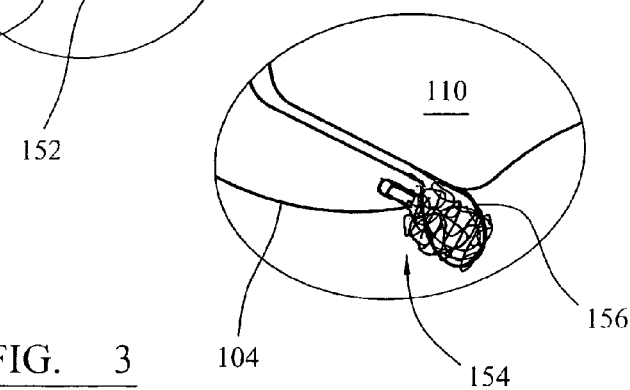
FIG. 3 shows a magnified view of a part of the implant and cement collector shown in FIG. 2.

FIG. 3 shows a view of an enlarged condylar portion of the implant and bone shown in FIG. 2. The condylar portion of the implant 104 is located toward the rear of the patient's knee joint. A portion 154 of the cement collector located on the rear facing part of the implant is positioned so that in use, when the implant is pressurised against bone cement, bone cement squeezed out from between the implant and bone is collected by the mesh.

In use, the bone is resected and otherwise generally prepared in a conventional manner. Bone cement is applied to the resected bone surface and then the implant 100 bearing the bone cement collector 150 is place on the bone and pressurised. Pressurisation of the implant causes the egress of bone cement at a number of locations around the periphery of the implant. However, the bone collector allows the excess bone cement to escape from the gap between the implant and the bone surface and pass into the mesh. The mesh also acts to trap and hence collect the excess bone cement owing to the tortuous paths through the voids in the mesh and the large surface area presented by the material of the mesh both restricts movement of cement through the mesh and also provides a large surface area to which the bone cement can begin at least partially to adhere. After a short wait of a few minutes, to allow the bone cement to continue curing, the surgeon can pull on a free end of the bone cement collector and release the cement collector from the implant using a tearing motion. The bone cement trapped in and by the mesh breaks away cleanly from the cement mantel between the implant and bone and is retained in and on the mesh thereby preventing or reducing the amount of bone cement left on the implant or bone or in the joint space.

FIG. 4 shows a further implant 120 bearing a further embodiment of a bone cement collector 160. The implant 120 is in the form of a tibial tray 122 and includes a plurality of holes 124 in a side wall and arranged around its periphery. The cement collector 160 is similar to that shown in FIGS. 1 to 3 in that it has a mesh body 162, but differs in that it has a plurality of male formations or pegs 164 positioned and dimensioned so as to mate with holes 124 in a push fit manner and provide a releasable attachment mechanism. By pulling on the cement collector 160 in the direction generally indicated by arrow 168, the cement collector can be removed from the implant in a generally tearing motion thereby removing any excess cement trapped on or in the mesh during use.

It will be appreciated that the cement collector can have a wide variety of form and can be releasably attached to a wide variety of implants using a wide variety of releasable attachment mechanisms.

For example, FIG. 5 shows a schematic perspective view of a further embodiment of a bone cement collector 170 also according to the invention and similar to that shown in FIG. 4. The bone cement collector has a body 172 made from a mesh or foam material, which is permeable to bone cement, and includes a peg 174, 176 at each end by which the bone collector 170 can be releasably attached to an implant via matching, mating holes.

FIG. 6 shows a schematic perspective view of a further embodiment of a bone cement collector 180 also according to the invention. The bone cement collector has a central support or substrate 184 from which a plurality of members or fingers 186 extend in a variety of different directions and in a generally cucumiform manner. The fingers and substrate provide a body which is generally permeable to bone cement, as it can pass between the fingers, but the fingers also act to trap bone cement and also provide a plurality of different or separate surfaces to which bone cement can adhere. A peg 188, 189 is provided toward each end by which the bone collector 180 can be releasably attached to an implant via matching, mating holes.

FIG. 7 shows a schematic perspective view of a further embodiment of a bone cement collector 190 also according to the invention. The bone cement has a body 192 in a generally spiral or coiled form. The coiled form of the body provides a body which is generally permeable to bone cement, as it can pass between the loops of the coil, but the loops of the coil can also act to trap bone cement and also provide a plurality of different or separate surfaces to which bone cement can adhere. A peg 194, 196 is provided toward each end by which the bone collector 190 can be releasably attached to an implant via matching, mating holes.

The cement collector can have a length selected to correspond to a region of the periphery of the implant at which cement egress is commonly experience in use.

Figures 8, 9, 10:
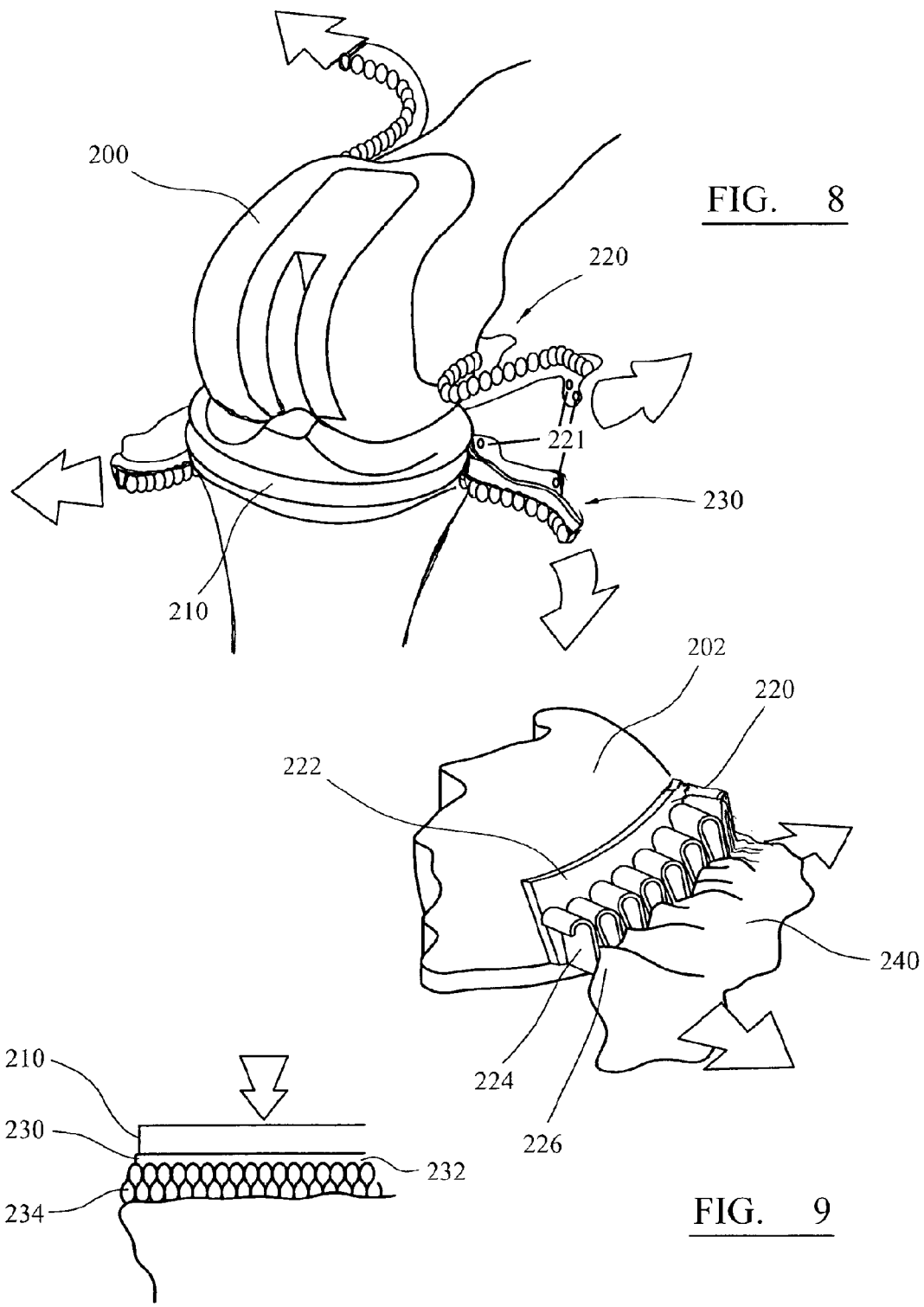
FIG. 8 shows a perspective view of a further implant and cement collector according to the invention.
FIG. 9 shows a perspective view of a femoral part of the implant shown in FIG. 8.
FIG. 10 shows a perspective view of a tibial part of the implant shown in FIG. 8.

FIG. 8 shows a further embodiment of implants 200, 210 and bone cement collectors 220, 230 according to the invention. A first implant 200 is a femoral implant and a second implant 210 is a tibial tray implant. FIG. 9 shows an enlarged view of a part 202 of the femoral implant 200 and FIG. 10 shows an expanded view of the tibial implant 210 in use. Each implant 200, 210 has a bone cement collector 220, 230 releasably attached to it. The bone cement collectors 220, 230 have a generally similar construction and are made from a suitable silicone material. The bone cement collectors each have a main support or substrate 222, 232 in the form or a ribbon or a band, with a plurality of suction cups (not shown) on a rear implant facing side. A cement permeable structure 224, 234 in the form of a concertina or folded strip is mounted on the substrate and defines a plurality of apertures, e.g. 226, toward a lower end thereof. The apertures defined by folded strip 224, 234 are positioned below the support 222, 232, so as to be located adjacent a region of the periphery of the implant from which bone cement 240 is likely to escape during use, as illustrated in FIG. 9.

The plurality of apertures provided by the folded strip make the bone cement collector permeable as bone cement can pass through it and the constriction caused by the material of the folded strip helps to trap bone cement within the collector and the walls of the folded strip provide a plurality of separate surface regions to which the bone cement can adhere. The suction cups provided on the rear surface of the collector co-operate with the shiny surface of the implant to provide a releasable attachment mechanism by the which collectors can be 'torn' from the implants to remove the excess bone cement captured therein in use, as illustrated by the arrows in FIG. 8.

It will be appreciated that there are a wide variety of modifications and changes and combinations of features which can be used in various embodiments of the invention beyond those described in detail above.

A wide variety of different releasable attachment mechanisms can be used. For example, various different types of mechanical mechanisms can be used, such as push-fit and snap fit mechanisms, such as snap in clips. None-mechanical mechanisms can also be used, such as various medical adhesives 221, including, for example, pressure sensitive adhesives, such as the ARcare 7261 adhesive as provide by Adhesives Research Inc.

A wide variety of different permeable body forms can be used to trap the cement. As well as the meshes and foams, nets, webs and other interlaced structures which define a plurality of voids having tortuous flow paths can be used. Various types of materials can be used, such as fabrics, gauzes, metals, alloys, plastics (including resorbable plastics such as PLA), silicones and similar.

The collector can have a one piece constructions and can extend around substantially the whole of the periphery of the implant of just around a part or parts of the periphery of the implant. The collector can be made up from multiple pieces which can extend around substantially the whole of the periphery of the implant of just around a part or parts of the periphery of the implant.

The collector can have handles in the form of strings or tabs extending from one or both the free ends of the collector and which a surgeon can grab and pull on in order to remove the collector from the implant. This is particularly helpful if the free ends of the collector are located toward a rearward facing part of the implant, in which case the handles can be located toward the front of the implant to help tear the collector from the implant by pulling on the handles.

The invention claimed is:

1. A bone cement collector for releasable attachment to an implant, the implant having a perimeter, comprising:
    a body having a flexible structure, the structure being permeable to bone cement and having openings or voids sized to trap bone cement, the body being elongate having a first end and a second end, the body being configured such that, when the first end and the second end are brought together about the perimeter of the implant, the body forms a substantially closed shape about the implant; and
    a releasable attachment mechanism attached to the body by which the body can be releasably attached to the implant, wherein at least one of the first end and the second end is configured to be grasped, the releasable attachment mechanism being configured to release from the implant when one of the first end and the second end is pulled away from the other of the first end and the second end and from the implant.

2. The bone cement collector of claim 1, wherein the releasable attachment mechanism comprises an adhesive.

3. The bone cement collector of claim 1, wherein the releasable attachment mechanism is a mechanical coupling.

4. The bone cement collector of claim 1, wherein the body comprises a substrate bearing at least one formation defining a plurality of voids or openings through which bone cement can pass.

5. The bone cement collector of claim 1, wherein the body collector comprises a substrate bearing at least one formation defining a plurality of separate surfaces to which bone cement can adhere.

6. The bone cement collector of claim 1, wherein the body is in the form of a strip.

7. The bone cement collector of claim 1, wherein the body is in the form of a ribbon.

8. The bone cement collector of claim 1, wherein the body is in the form of a band.

9. A bone cement controlling system, comprising:
an orthopaedic implant component having a perimeter;
a body having a flexible structure, the structure being permeable to bone cement and having openings or voids sized to trap bone cement, the body being elongate having a first end and a second end, the body being configured such that, when the first end and the second end are brought together about the perimeter of the implant, the body forms a substantially closed shape about the implant, and wherein at least one of the first end and the second end is configured to be grasped; and
a releasable attachment mechanism attached to the body by which the body can be releasably attached to the implant at a location on the implant at which bone cement escapes during placement of the orthopaedic implant, and wherein the releasable attachment mechanism is configured to release from the implant when one of the first end and the second end is pulled away from the other of the first end and the second end and from the implant.

10. The system of claim 9, wherein the bone cement collector extends at least partially about an end of the component intended to face rearward when the component is implanted.

11. The system of claim 9, wherein the bone cement collector extends substantially entirely around the perimeter of the component.

12. The bone cement controlling system of claim 9, wherein the body is in the form of a strip.

13. The bone cement controlling system of claim 9, wherein the body is in the form of a ribbon.

14. The bone cement controlling system of claim 9, wherein the body is in the form of a band.

15. A method for handling bone cement during an orthopaedic arthroplasty procedure, comprising the steps of:
applying bone cement to a prepared surface of a bone;
providing an implant component having releasably attached thereto a body having a flexible, elongate structure about a perimeter of an implant component, the structure being permeable to bone cement and having openings or voids sized to trap bone cement, the elongate body having a first end and a second end which are positioned adjacent one another, thereby forming said elongate structure into a substantially closed shape about the implant;
positioning the implant component having the body attached thereto in contact with the bone cement;
grasping one of the first end and the second end of the body;
pulling said one of the first end and the second end away from the other of the first end and the second end so as to release the body from the implant component;
removing the body, and any cement attached thereto, from the implant component; and
leaving the implant component in its position in contact with the bone cement.

16. The method of claim 15, wherein removing the body from the implant component includes removing at least a portion of the body from a rearward facing portion of the implant component.

* * * * *